US00PP20383P2

(12) United States Plant Patent
Feng

(10) Patent No.: US PP20,383 P2
(45) Date of Patent: Oct. 6, 2009

(54) ***PHALAENOPSIS* PLANT NAMED 'SOGO F1582'**

(50) Latin Name: ***Phalaenopsis* orchid**
Varietal Denomination: SOGO F1582

(76) Inventor: Chiang-Kuei Feng, No.1-1, Chenggong Xincun, Jiyang Village, Meinong Town, Kaohsiung County (TW)

( * ) Notice: Subject to any disclaimer, the term of this patent is extended or adjusted under 35 U.S.C. 154(b) by 0 days.

(21) Appl. No.: 12/151,459

(22) Filed: May 7, 2008

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para

(74) *Attorney, Agent, or Firm*—Frenkel & Associates, P.C.

(57) ABSTRACT

A new and distinct cultivar of *Phalaenopsis* plant named 'SOGO F1582', comprises its flowers of white border with pink overlaid toward pink base and the pink white labellum, freely flowering habit, upright, freely branching and sturdy flowering stems, and the excellent postproduction longevity.

2 Drawing Sheets

FIELD OF THE INVENTION

Botanical classification/cultivar designation: *Phalaenopsis* Orchid cultivar SOGO F1582.

BACKGROUND OF THE INVENTION

The present invention comprises a new and distinct cultivar of *Phalaenopsis* Orchid, a bigeneric hybrid of *Phalaenopsis*× *Phalaenopsis* of the family Orchidaceae, and hereinafter referred to as the cultivar name, 'SOGO F1582'. The genus *Phalaenopsis* is a member of the family Orchidaceae.

*Phalaenopsis* comprise a group of bigeneric hybrids generally intermediate in character between the parent genera, which are suitable for cultivation in the home or greenhouse. The parent genera of *Phalaenopsis* are predominantly epiphytic or rock dwelling, and are native to tropical Asia, Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

*Phalaenopsis* orchid, often referred to 'Moth Orchids' in the horticultural trade, are frequently used to furnish cut flowers for the florist trade, or sold as flowering potted plants for home or interiorscape.

*Phalaenopsis* produce upright racemes, often with many showy flowers, which open in succession beginning with the lowermost. The flowers possess three sepals, and three petals, the lateral ones being alike. The lowermost petal, called the labellum, is three lobed and is often more brightly colored than other flower segments. Flower colors are frequently various shades of pink, white and yellow.

*Phalaenopsis* orchids are typically propagated from seeds. However, *Phalaenopsis* is capable of being asexually reproduced from offshoots, which frequently arise from the lower bracts of the inflorescence. The resulting plants are detached from the mother plant and may be planted in a suitable substrate.

'SOGO F1582' is a product of a planned breeding program conducted by the inventor in Kaohsiung County, Taiwan, R.O.C. The objective of the breeding program is to create new uniform pot-type *Phalaenopsis* Orchid cultivars having attractive flower coloration. The inventor has addressed himself to Orchids breeding since 1985.

'SOGO F1582' was discovered by the inventor from within the progeny of a cross-pollination of one *Phalaenopsis* Orchid, *Phal.* 'Hilo Lip' and one *Phalaenopsis* Orchid, *Phal.* 'Schilleriana' on February 1999, in a controlled environment in Kaohsiung County, Taiwan, R.O.C.

Asexual propagation by tissue culture in a laboratory in Pingdong County, Taiwan, R.O.C. has been used to increase the number of plants for evaluation and has demonstrated in a controlled environment in Kaohsiung County, Taiwan, R.O.C. that the unique combination of characteristics as herein disclosed for the new *Phalaenopsis* Orchid are firmly fixed and are retained through successive generations of asexual reproduction.

SUMMARY OF THE INVENTION

The following traits have been repeatedly observed and are determined to be basic characteristics of 'SOGO F1582' which in combination distinguish this *Phalaenopsis* Orchid as a new and distinct cultivar:

1. White border with pink overlaid toward base and the pink white colored labellum.
2. Freely flowering habit.
3. Upright, freely branching and sturdy flowering stems.
4. Excellent postproduction longevity.

Plants of 'SOGO F1582' differ primarily from plants of parent cultivars in flower color. The main color of the petals of *Phal.* Hilo Lip is RHS N75D. Since the flower thereof is monochromatic, there is no pattern color. The main color of the petals of *Phal.* Schilleriana is RHS 76C, and the pattern color thereof is RHS N76A.

Currently, there is no commercial cultivar to which 'SOGO F1582' can be meaningfully compared.

BRIEF DESCRIPTION OF THE DRAWINGS

The accompanied photographic illustrations show typical plant and flower characteristics of 'SOGO F1582' with colors being as true as possible with illustrations of this type.

DETAILED DESCRIPTION OF THE PREFERRED EMBODIMENTS

Figure 1:
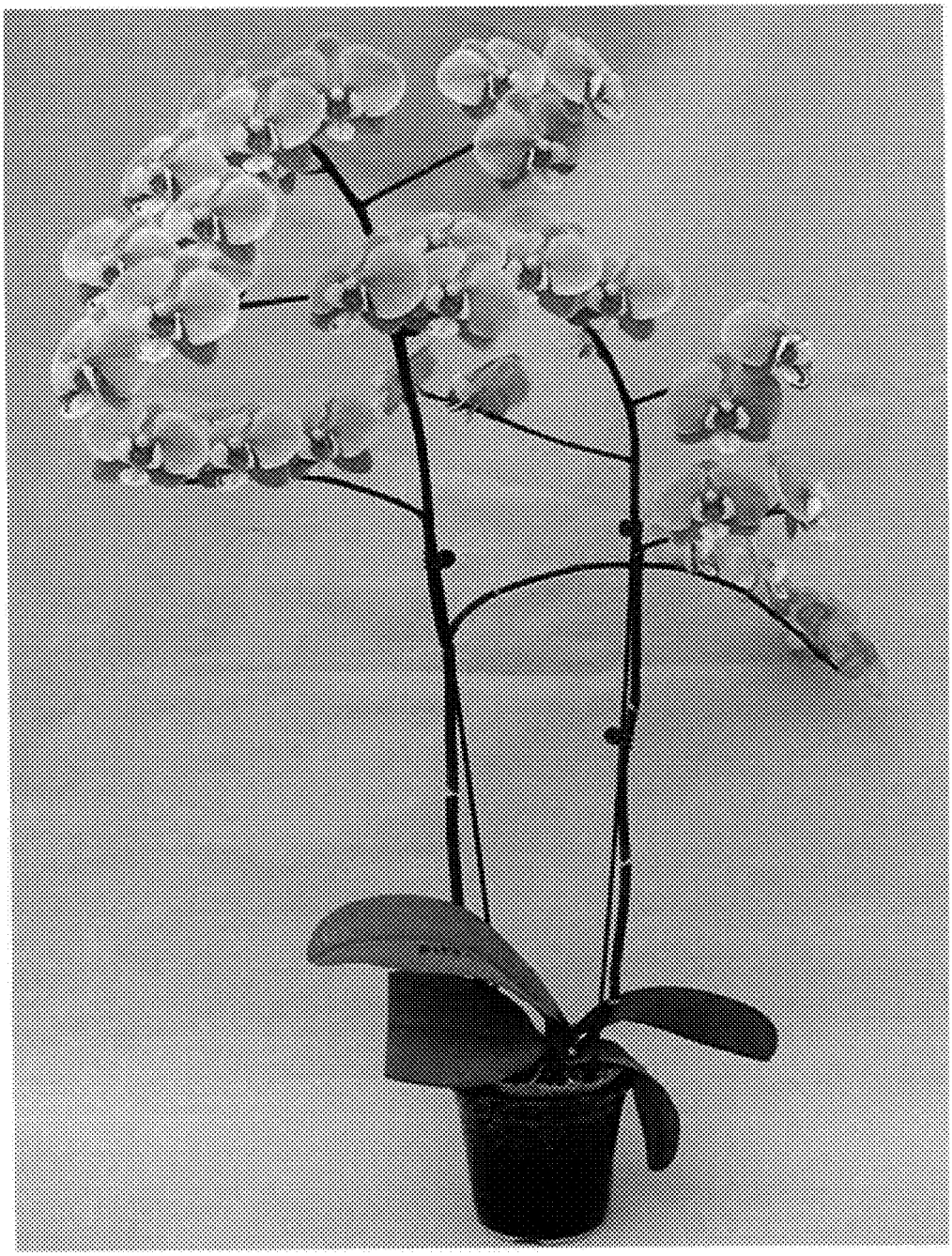
FIG. 1 is a side view of a plant of 'SOGO F1582' flowering in the pot of 13 cm.
Figure 2:
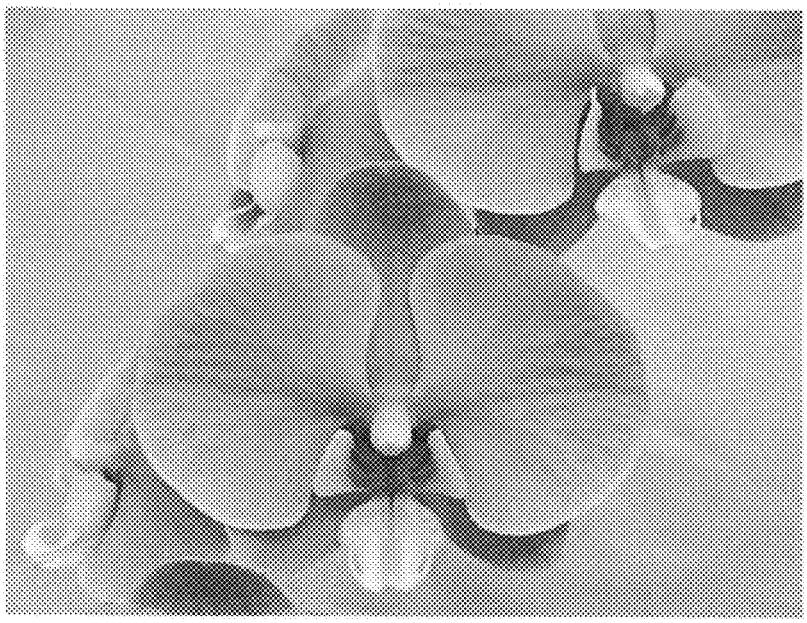
FIG. 2 is a close-up view showing the characteristics of the flower.
Figure 3:
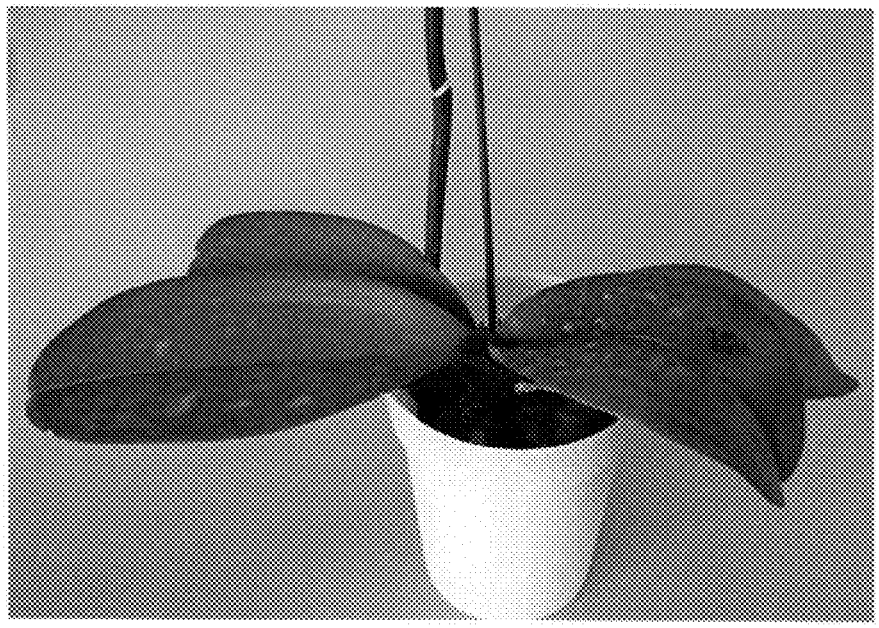
FIG. 3 is a close-up view showing the characteristics of the leaf.

'SOGO F1582' has not been observed under all possible environmental conditions. The phenotype may vary significantly with variations in environment such as temperature, light intensity, fertilization and day length without any change in the genotype.

The observations and measurements describe plants grown in Kaohsiung County, Taiwan, R.O.C. under the conditions, which approximate those generally used in commercial practice.

In the following description, color references are made to The Royal Horticultural Society (R.H.S.) Colour Chart.

Plants used for the aforementioned photographs and the following detailed botanical description were 18 months in maturity and grown in the pots of 13 cm, in a controlled greenhouse with day-night temperature around 25–18 degree Celsius, and light intensity between 15,000~20,000 lux natural light, in Kaohsiung County, Taiwan, R.O.C.

Origin: Seedling from a cross of the selected *Phalaenopsis* orchids described above.

Classification: *Phalaenopsis* hybrid cv. 'SOGO F1582'.

Propagation: Asexual propagation by tissue culture.

Plant description:

*Plant height.*—Soil level to top of foliar plane is about 5 to 10 cm.

*Plant height.*—Soil level to top of inflorescences is about 65 to 75 cm.

*Plant diameter.*—Is about 38 to 43 cm.

*Growth habit.*—Compact, small, dark-green leaves and a relatively short raceme.

*Flowers per stem.*—Approximately 25 to 30.

Foliage description:

*Quantity.*—Approximately 6 to 8 leaves are produced before flowering.

*Size of leaf.*—18 to 23 cm long and 8 to 10 cm wide.

*Shape.*—The leaf blade is short and elliptic with a cuneate base and an obtuse tip. The leaf blade is leathery and thick. The middle vein protrudes, while the other veins are not visible in the thick leaf blade.

*Attitude.*—Horizontal and on two sides parallel.

*Color.*—Upper surface: Dark-green, RHS 146A. Lower surface: Red-Purple, RHS 59A.

Inflorescence description:

*Flower type and habit.*—Single zygomorphic flowers arranged in racemes. Flowers are roughly pentagonal in shape. Flowering stems upright, freely branching and sturdy. Plants freely flowering; plants typically produce one to three branched flowering stems with at least 20 to 25 flowers each.

*Fragrance.*—No fragrance.

*Natural flowering season.*—From February to April in the southern part of Taiwan. The flower spikes can be induced under the controlled environment, of which day-night temperature at 25–18 degree C. for 2 weeks.

*Post-production longevity.*—Plants of 'SOGO F1582' maintain good leaf and flower substance for about three to six months on the plant under interior environmental conditions. Lastingness of cut flowers has not been observed.

*Inflorescence length.*—About 45 to 50 cm.

*Inflorescence diameter.*—About 50 to 55 cm.

*General impressions of petals and sepals.*—Horizontal elliptical in shape, about 8.2 cm of flower width in front view.

*Sepals.*—There are 3 sepals which are fleshy and glabrous in texture, with straight margins and in elliptical shape, about 3.4 cm in length and 3.4 cm in diameter. The main color of dorsal sepal is RHS N81D, the pattern color of dorsal sepal is N80B. The main color of lateral sepals is RHS N81D, the pattern color of lateral sepal is N80B.

*Petals.*—There are 2 open petals which are fleshy and glabrous in texture, with margins weakly undulate and in elliptical shape, about 3.8 cm in length and 4.8 cm in diameter. The main color of petals is RHS N74D, the pattern color of petals is N74D.

*Labellum* (*lip*).—The lip whiskers are absent, shape of apical lobe is ovate, approximately 2.3 cm long and 2.1 cm wide. The base color of apical lobe is RHS 76D, the tip color of apical lobe is RHS 76D.

*Peduncles.*—Length about 80 to 90 cm, diameter about 7 mm, upright, strong and sturdy, with smooth and glabrous texture. Color is RHS N79B.

*Pedicels.*—Length about 4.5 cm, diameter about 4 mm. Aspect about 95 degree from vertical. Strong, with a texture of smooth and glabrous. Color RHS 76C, towards the base, overlaid with RHS 147C.

Reproductive organs: The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Approximately 10 mm long and 7 mm wide, RHS 76B.

*Pollinia.*—Two, about 1.5 mm oval masses of pollen present, RHS 24A.

*Ovary.*—6 to 8 mm long and 2.5 mm in diameter, RHS 75B.

Roots: Fleshy, approximately 6 mm wide and green, RHS 189A.

Plant disease resistance/susceptibility: No specific resistance or susceptibility observed.

General observations: *Phalaenopsis* 'SOGO F1582' produces two or more inflorescence with flowers having sepals and petals in the color of white border with pink overlaid toward base. A pink white labellum. The inflorescence is strong, erect and sturdy, relatively short, and easily packaged for shipping. The plant grows very quickly to marketable size. 'SOGO F1582' can be economically propagated via tissue culture.

What is claimed is:

1. A new and distinct cultivar of *Phalaenopsis* orchid plant named 'SOGO F1582' as illustrated and described.

* * * * *